United States Patent [19]

Fuchs et al.

[11] Patent Number: 5,075,235
[45] Date of Patent: Dec. 24, 1991

[54] PROCESS FOR DIRECT DETERMINATION OF COMPLEX CORROSIVE ENVIRONMENTAL CONDITIONS

[75] Inventors: Dieter Fuchs, Veitshöchheim; Gelmut Patzelt, Marienrachdorf; Gerhard Tünker, Duisburg, all of Fed. Rep. of Germany

[73] Assignee: Fraunhofer-Gesellschaft Zur Forderung der Angewandten Forschung E.V., Munich, Fed. Rep. of Germany

[21] Appl. No.: 313,455

[22] Filed: Feb. 22, 1989

[30] Foreign Application Priority Data

Feb. 22, 1988 [DE] Fed. Rep. of Germany ....... 3805495

[51] Int. Cl.$^5$ ...................... G01N 17/00; G01N 17/04
[52] U.S. Cl. ........................... 436/6; 422/53
[58] Field of Search ............................. 436/6; 422/53

[56] References Cited

PUBLICATIONS

Gilles et al., "Decay of Medieval Stained Glass at York, Canterbury and Carlisle, I: Composition of the Glass and its Weathering Products", Glastechnische Berichte, 1988 61(3) 75-84 (Abstract Only).
Stephanowitz, "IR Reflection Investigation of Corrosion of Optical Glasses", Wiss. Z. Friedrich-Schiller-Univ. Jena, Math. Naturwiss, Rethe vol. 31, No. 6, pp. 1017-1023.
Dilmore, et al, Journal of The American Ceramic Society, vol. 6, No. 9-10 Sep.-Oct. 1978.
Sanders et al., "Mechanism of Glass Corrosion", Journal of The American Ceramic Society, vol. 56, No. 7, Jul. 1973.
Tregant et al., "Comparative Corrosion Mechanism of THF1/4 and ZrF1/14 Based Fluoride Glasses in Aqueous Solution", Journal of Non-Crystalline Solids vol. 83, No. 3, Jul. 1, 1986, pp. 282-296.
Mostowaya et al, "Corrosion of the Surfaces of Polished Glass" Glass and Ceramics vol. 43, No. 1-2 Jan.-Feb. 1986 pp. 21-24.

Primary Examiner—Robert J. Warden
Assistant Examiner—Lyle A. Alexander
Attorney, Agent, or Firm—Oblon, Spivak, McClelland, Maier & Neustadt

[57] ABSTRACT

A process is described for direct determination of complex corrosive environmental conditions, which comprises exposing a glass surface to the environment and examing the glass surface before and after exposure using a measurement method based on radiation, in particular a IR-spectroscopic method, in order to determine corrosion effects, in particular water absorption and ion exchange. Glass sensors suitable for use in this process are likewise described.

10 Claims, 1 Drawing Sheet

PROCESS FOR DIRECT DETERMINATION OF COMPLEX CORROSIVE ENVIRONMENTAL CONDITIONS

BACKGROUND OF THE INVENTION

In recent years, the population has become increasingly aware of atmospheric pollution by pollutants, for example sulfur dioxide, nitrogen oxides, carcinogenic organic compounds, etc., and the damage increasingly caused by these substances, not only in nature but also on buildings, monuments and the like. In attempting to preserve as well as possible works of art and other objects of cultural or art-historical interest for future generations in spite of the adverse environmental conditions, a very wide variety of preservation measures have been taken and, of course, particular attempts have been made to screen valuable objects against corrosive environmental conditions. Thus, external protective glazing, for example, is the method which is customary today for protection of historical, corrosion-endangered glass paintings, in particular in medieval church windows.

However, it is not easy to determine the extent to which screening of this type actually fulfills the expectations which are made of them. The most reliable method would undoubtedly be direct examination of the object to be protected for corrosion effects. However, this can in most cases only be carried out with difficulty or not at all since examinations of this type must generally not be carried out on site but instead in the laboratory, which causes transport problems; in addition, these examinations are usually not possible without damaging the object under investigation. Due to the long observation times necessary and due to analytical problems (non-reproducible surface conditions, submicroscopic nature of the primary corrosion processes, etc.), neither is it generally possible to directly assess the protective action actually achieved by analyzing the progress of corrosion on the actual object to be protected. For this reason, numerous research projects have hitherto been carried out on the indirect determination of corrosive conditions with reference to relevant climatic data, for example humidity and temperature. However, it is common to all these investigations that only peripheral climatic conditions have been determined, but, due to the complex and as yet substantially unexplained corrosion mechanisms, it is not possible to come to any direct conclusions on the corrosive situation on the surface of the object of interest. In addition, very considerable equipment costs are necessary for this purpose, which are generally too expensive for practical use. Thus, each environmental factor whose effect on the corrosion process is to be taken into account must be determined individually, which means that, taking into account subclimatic differences, a large number of measurements and measurement sensors is necessary, even if only a single object is to be examined.

SUMMARY OF THE INVENTION

There is thus a demand for an inexpensive, technically uncomplicated and reliable process for direct determination of complex corrosive environmental conditions. The object of the present invention is to provide such a process. This object is achieved according to the invention by a process for direct determination of complex corrosive environmental conditions which comprises exposing a glass surface to the environment to be investigated and examining this glass surface before and after exposure to a measurement method based on radiation in order to determine corrosive effects, in particular water absorption and ion exchange.

DESCRIPTION OF THE PREFERRED EMBODIMENT

Figure 1:
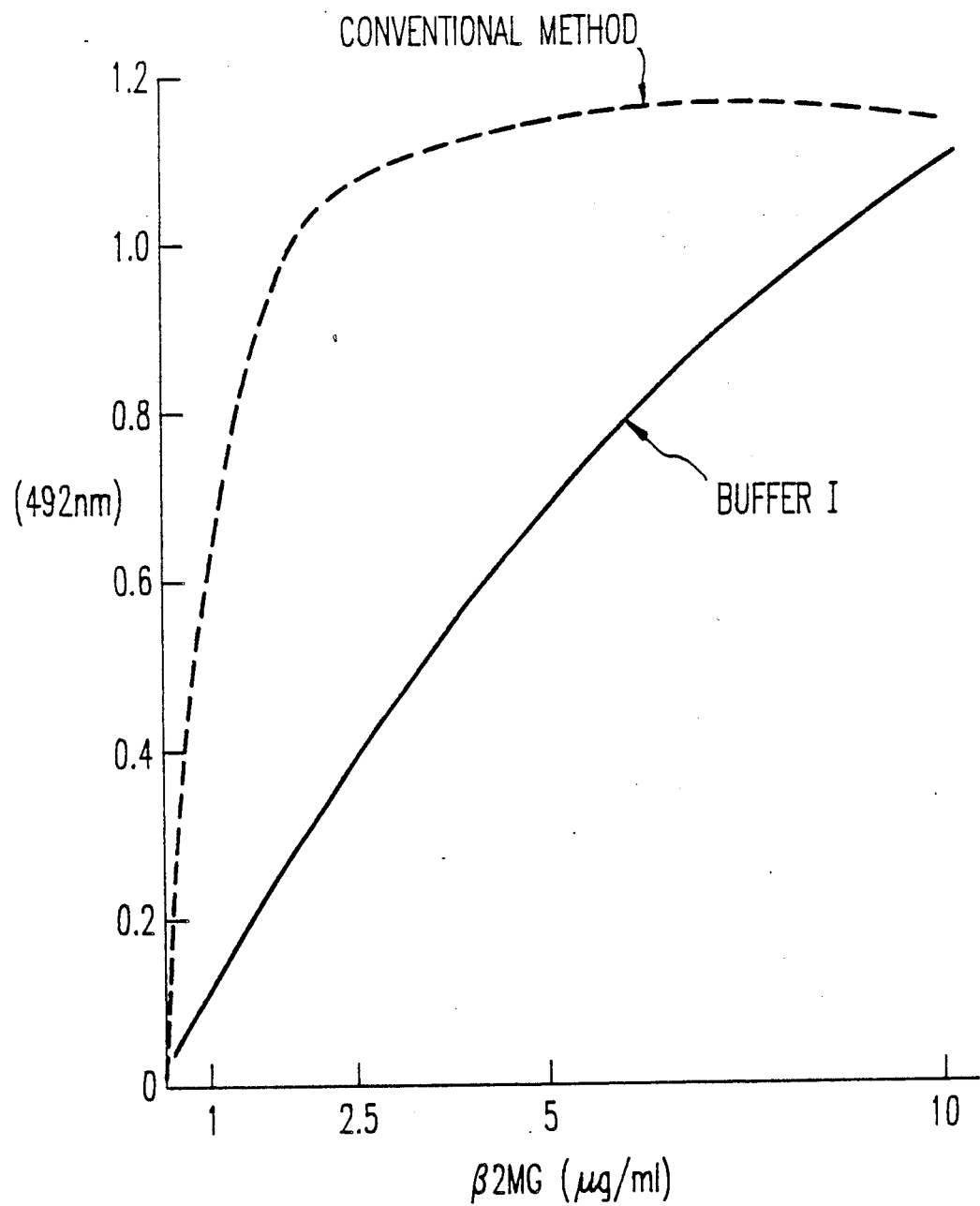
FIG. 1 shows the increase in the OH vibration band for corroded glass.
Figure 1:
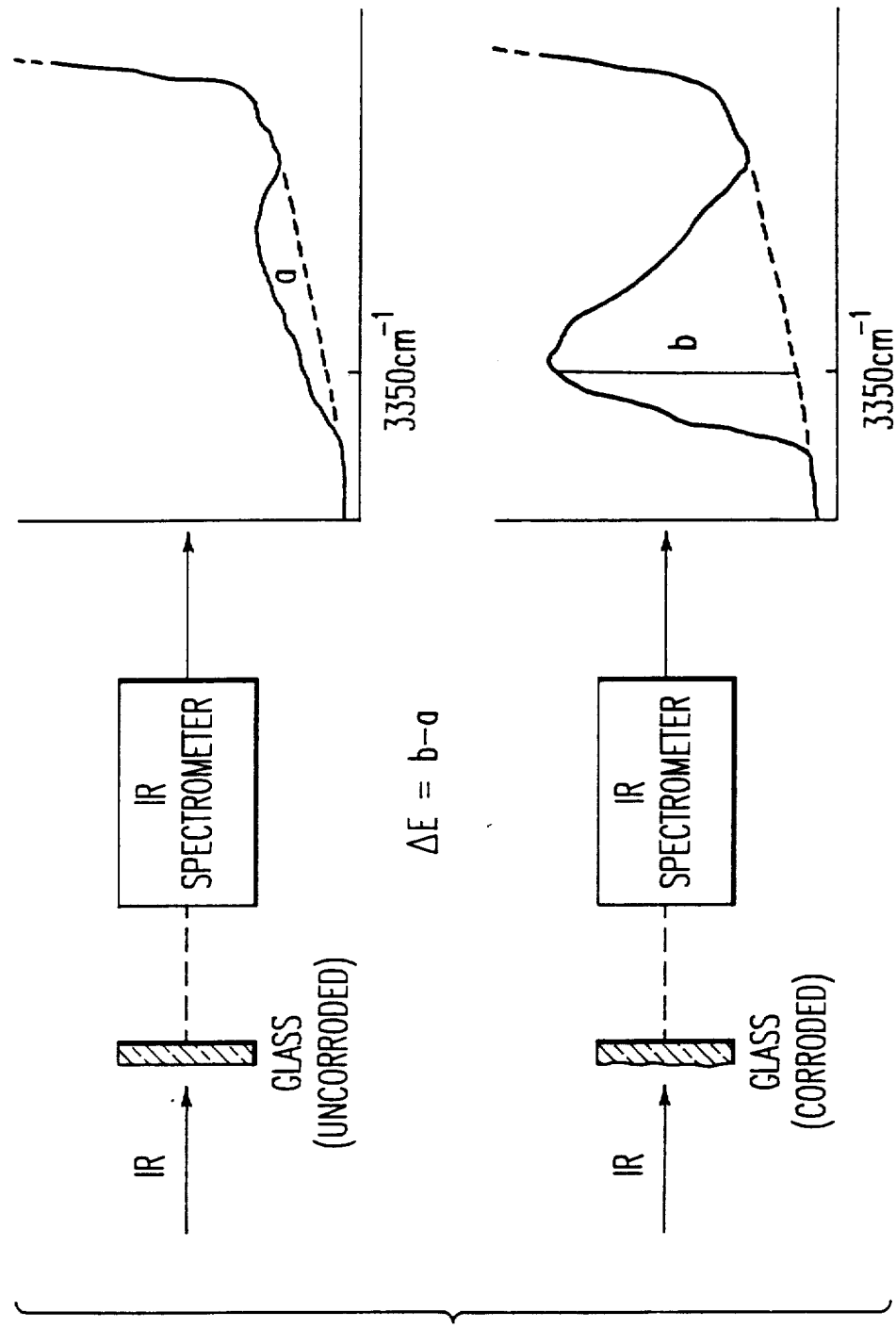

Suitable measurement methods based on radiation are, in principle, all known processes, such as, for example, IR, UV, NMR and PES spectroscopic and (electronic) microscopic studies. Measurement processes using X-rays and other methods which are suitable for characterization of surfaces can also be employed according to the invention. From the point of view of low equipment cost and easy evaluation of the results obtained, IR spectroscopic methods are preferred.

According to particularly preferred embodiments of the present invention, the glass surface is examined by IR spectroscopy before and after contact with the corrosive environmental conditions with respect to the increase in the intensity of the OH vibration bands. Expediently, the simplest procedure is to measure the difference $\Delta E$ of the extinction at about 3350 cm$^{-1}$, the absorption maximum of the OH vibration of water, before and after exposure (see FIG. 1). The increase in the extinction is proportional to the absorption of water by the glass surface and is therefore a very reliable measure of the progress of the corrosion process.

It is known that glass reacts differently to corrosive environmental factors depending on its composition, in particular its content of $SiO_2$, $K_2O$ and $CaO$. In order to obtain the most reliable picture possible of the corrosive environmental conditions, it is accordingly preferred according to the invention to carry out parallel investigations on glass surfaces of different chemical composition. Depending on the composition of the glass, it is thereby possible to obtain both information on the time dependency of the corrosion and on the level of pollution by factors causing the corrosion.

Since corrosion caused by environmental factors is a relatively slow process, it is expedient to expose the glass surface to the corrosive environmental conditions for a period of time which is sufficient to cause changes to the glass surface which are considerable and easy to detect spectroscopically. Although this period of time is naturally essentially dependent on whether the glass is sensitive to corrosive conditions or less sensitive and on the extent to which corrosive factors are present, a period of time of at least three months is advisable. A period of time of at least six months is more preferred. In order to be able to include seasonal variations in with the corrosive environmental factors, it may even be necessary to expose the glass surface to the corrosive conditions for one year or more. In principle, the exposure duration has no upper limit. However, it should be taken into account that sensitive glasses corrode relatively rapidly, causing flaking-off of the outermost layers of the surface to commence sooner or later, thus distorting the measurement results.

The process according to the invention gives particularly informative results if it is used to investigate corrosion processes on glass objects, for example on historical glass windows, since the glass surface can in this case, inter alia, be chosen to be one the composition of which corresponds to the composition of the historical glass and direct conclusions on corrosive effects on the surface of the object of interest are thereby possible without the latter itself having to be transported and examined. The compositions of historical glasses, in particular medieval glasses, can be discovered from the literature, for example C. J. Iliffe and R. G. Newton, "Using triangular diagrams to understand the behavior of medieval glass", Verres Refract., 30 (1976) 30 to 34.

To carry out the process according to the invention, a glass sensor is preferably used which comprises one or more glass plates if appropriate held in a frame or fixed in another manner, of a thickness of from 0.1 to 10 mm, preferably 0.25 to 1 mm, whose rear side is covered essentially gas-tight using metal, plastic and/or glass. These sensors are suitable, in particular, for IR spectroscopic studies. The covering of one surface of the glass plates is advantageous since only one surface is thereby exposed to the corrosive environmental conditions. If both glass surfaces were freely accessible, the sum of the water absorption on the front and rear sides would be measured in the subsequent IR spectroscopic study. Since the environmental conditions may be different on the front and rear sides, depending on the type and manner of mounting of the glass sensor, only the mean value of these environment conditions would thereby be determined. Of course, it is in principle not necessary to cover the rear side if the environment conditions are absolutely identical on both the front and rear side of the glass plate. The rear side can be covered, for example, by sticking on an aluminum foil or plastic film. If the entire surface of the rear side is covered, this covering must be removed in a suitable manner before the glass plate is introduced into the IR spectrometer if the covering is impermeable to IR radiation. It is also possible to provide a small opening in the covering (for example in the aluminum foil) and to mount a corrosion-resistant glass on this covering in a suitable manner so that the free surface on the rear of the glass sensor is screened from the corrosive environmental conditions. In this case, removal of the covering before measurement is superfluous.

The glass plates of the glass sensor according to the invention can be produced, for example, by melting the glass components in a manner known per se, preferably to form block glass, and then cutting this block into sheets of the desired thickness. In this case, it must be noted that the surface of these sheets must generally be mechanically polished, which somewhat reduces the thickness of the sheets or plates. The surface of the plates should be as smooth as possible since undesired scattering effects occur if the surface is rough. It should also be ensured that the composition at the surface is very homogeneous since the surface is examined twice in the process according to the invention (once before and once after exposure), and the two measurements are generally not carried out at exactly the same point of the surface, which means that any inhomogeneity of the surface would have the danger of distorting the measurement results (as stated above, the corrosion behavior also changes with the chemical composition of the surface).

Instead of by mechanical polishing, the surface can also be rendered smooth and homogeneous by many other methods which are suitable for this purpose, for example by flame melting.

It is of course also possible to apply the glass surface to be investigated to a (preferably transparent) substrate, for example by melting-on, vapor deposition, the sol-gel process, and other known processes which are suitable for this purpose. The thickness of the surface coating here should preferably be within the range indicated for glass plates of homogeneous composition. In this case, a particularly suitable substrate material is a resistant glass.

According to the invention, the glass sensors have glass plates of a thickness of from 0.1 to 10 mm. These limits for the dimensions are stipulated exclusively by practical considerations. At a lower thickness than 0.1 mm, the glass plates become so difficult to handle that they can only be transported if considerable safety measures are taken. A thickness of greater than 10 mm is uneconomic and makes the measurements to be carried out more difficult. A thickness of the glass plate in the range of from 0.25 to 1 mm, in particular 0.4 to 0.6 mm, is particularly preferred.

The glass plates or glass sensors can in principle have any desired size. However, the exposable glass surface should generally be not less than 0.25 $cm^2$, preferably not less than 0.5 $cm^2$. There is in principle no upper limit to the size of the glass surface. Not least for economic considerations, however, this area is generally chosen to be as small as possible, and it should also be taken into account that the smaller the dimensions of a glass sensor, the more inconspicuously it can be mounted.

As already stated above, it is usually advantageous to carry out parallel investigations on glasses of different composition. To this end, several separate glass sensors can be used or the glass sensor as such already contains glass plates of different composition. This is of advantage since it is thus ensured that all the glasses investigated were exposed to exactly the same environment.

It is known that the corrosion stability of glasses increases with their $SiO_2$ content. In contrast, glasses having a high potassium and calcium content are particularly susceptible to corrosive environmental conditions. Accordingly, variation of the amounts of the components just mentioned have a great effect on the properties and the corrosion behavior of the particular glass. Thus, for example, it has been found that a certain glass type reacts very rapidly to acidic harmful gases and $\Delta E$ (at 3350 $cm^{-1}$) changes proportionally to t in the IR spectrum (the corrosion proceeds rapidly with time). A glass of this type has the following composition:
43 to 52 percent by weight of $SiO_2$
20 to 30 percent by weight of $K_2O$
12 to 18 percent by weight of CaO
and at least one of the oxides $Na_2O$, MgO, $Al_2O_3$ and $P_2O_5$ in a total amount of from 9 to 15 percent by weight.

The glass A having the following composition is representative of a glass of this type: 48.0 percent by weight of $SiO_2$, 25.5 percent by weight of $K_2O$, 15.0 percent by weight of CaO, 3.0 percent by weight of $Na_2O$, 3.0 percent by weight of MgO, 1.5 percent by weight of $Al_2O_3$ and 4.0 percent by weight of $P_2O_5$.

On high exposure, another glass type exhibits only progress of corrosion as far as a certain corrosion level, at which weathering then stagnates. The "height" of this level, which can be determined very accurately by the IR method, varies with the level of the corrosive exposure parameters and can therefore be used as an indicator in strongly corrosive conditions. This glass type has the following composition:
50 to 70 percent by weight of $SiO_2$
10 to 20 percent by weight of $K_2O$
20 to 30 percent by weight of CaO
and optionally at least one of the oxides $Na_2O$, MgO, $Al_2O_3$ and $P_2O_5$ in a total amount of up to 10 percent by weight.

A concrete example of this glass type is the glass B, having the following composition: 60.0 percent by weight of $SiO_2$, 15.0 percent of $K_2O$ and 25.0 percent by weight of CaO.

The use of different glass types at the same location thus provides different and mutually complementary information on the corrosive environment conditions prevailing at this point.

The use of different glasses of different sensitivity is also advisable since it is thereby ensured that glasses which can be evaluated are always present, even if individual glasses have already become unusable as a consequence of their sensitivity (for example by cracking and flaking of the surface).

The glass sensors according to the invention can be mounted in any desired manner, for example by pinning, sticking, suspending, tying, etc. Of course, other determinations, in particular those which are likewise based on irradiation, can be carried out instead of or in addition to the IR investigation of the glass sensors. Thus, for example, photoelectron spectroscopy can provide important information on the leaching of (alkali and alkine earth) metal ions at the surface (depth of leaching). Studies using a scanning electron microscope and X-ray studies of the surface can also provide important (additional) information on the corrosion processes. Measurements of the loss in transparency of the glass plates after exposure is also a simple and informative investigative method.

An essential advantage of the process according to the invention is that corrosive factors which can only be determined with difficulty by other methods, for example the promotion of corrosion processes by microorganisms on the surface of the object of interest, can also be taken into account.

An important area of application of the process according to the invention is the investigation of the effectiveness of protective measures, in particular of the external protective glazing of historical windows, for example church windows. Introduction of the glass sensors according to the invention into the space between original glazing and external protective glazing, which is usually readily possible from the inside of the original glazing, and the investigation of these glass sensors before and after introduction allows reliable information to be obtained on the corrosive conditions in this space, and direct conclusions on the effectiveness of the protective measures in relation to the original glazing are possible if a glass plate is used whose composition corresponds to the composition of the original glazing. If in accordance with the invention, it is also possible, by comparing the results obtained with glass sensors mounted on the one hand and on the other hand after constructional corrosional-protection measures (for example external protective glazing), to estimate in a concrete case the protective (screening) effect which has actually been achieved (see example).

The ease of mounting the sensors according to the invention is also of advantage, since it is thereby possible to carry out a determination at different points of the protective structure and of the edifice. Additional object-specific detailed information can thus be obtained.

In summary, the process according to the invention has many advantages, and makes it possible, in particular, to determine complex corrosive environmental conditions and their effects on a particular corrosion-endangered object simply and at the same time very reliably.

The example below illustrates the present invention.

With the aid of glass sensors comprising 2 glass plates of different chemical composition (A and B, see above), investigations of the church windows were carried out at each of three churches (St. Lorenz, Nuremburg, St. Jans, Gouda, and the Minster, York). To this end, sensors were mounted both on the outside of the protective glazing and in the space between the protective glazing and the original glazing. After one year, the $\Delta E$ values were determined at 3350 $cm^{-1}$ in the IR spectrum. The results are shown in the table below. These results illustrate not only the different response of the two model glasses to the particular environmental conditions, but also show that the protective glazing results in a considerable reduction in the corrosion factors. Nevertheless, it is clear that corrosion is also continuing to a non-negligible extent on the (apparently reliably protected) outside of the original glazing, meaning that further protective measures are necessary.

TABLE

| | $\Delta E$ values for glass A(B) | |
|---|---|---|
| | Outside of the protective glazing | Space between the protective glass and the original glass |
| St. Lorenz Nuremburg | 0.72 (0.07) | 0.07 (0.03) |
| St. Jans Gouda | 0.70 (0.07) | 0.04 (0.01) |
| Minster York | 0.40 (0.11) | 0.07 (0.02) |

What we claim is:

1. A process for direct determination of complex corrosive atmospheric environmental conditions, which comprises exposing one or more glass surfaces to the atmospheric environment and examining said glass surfaces before and after exposure using radiation examination of the glass in order to determine corrosion effects such as water absorption and ion exchange, at least one of said glass surfaces initially having one of the following compositions:
   (a) 43 to 52% by weight of $SiO_2$, 20 to 30% by weight of $K_2O$, 12 to 18% by weight of CaO, and at least one of the oxides selected from $Na_2O$, MgO, $Al_2O_3$ and $P_2O_5$ in a total amount of from 9 to 15% by weight; and
   (b) 50 to 70% by weight of $SiO_2$, 10 to 20% by weight of $K_2O$, 20 to 30% by weight of CaO, and, optionally, one or more oxides selected from $Na_2O$, MgO, $Al_2O_3$ and $P_2O_5$ in a total amount of up to 10% by weight.

2. The process as claimed in claim 1, wherein the corrosion effects are determined by examining more than one glass surfaces of different chemical composition.

3. The process as claimed in claim 1, wherein the glass surface is exposed to the environment for at least three months, preferably for at least six months.

4. The process as claimed in claim 1, wherein the radiation examination is an IR spectroscopic method.

5. The process as claimed in claim 4, wherein the increase in the strength of the OH vibration bands in the IR spectrum is measured, preferably, by determining the extinction at about 3350 cm$^{-1}$.

6. A glass detecting device which comprises one or more glass plates of a thickness of from 0.1–10 mm, whose rear side is covered essentially gas-tight with metal, plastic or glass or a combination thereof which glass detecting device comprises a glass plate having one of the following compositions:
  (a) 43 to 52% by weight of $SiO_2$, 20 to 30% by weight of $K_2O$, 12 to 18% by weight of CaO, and at least one of the oxides selected from $Na_2O$, MgO, $Al_2O_3$ and $P_2O_5$ in a total amount of from 9 to 15% by weight; and
  (b) 50 to 70% by weight of $SiO_2$, 10 to 20% by weight of $K_2O$, 20 to 30% by weight of CaO, and, optionally, one or more oxides selected from $Na_2O$, MgO, $Al_2O_3$ and $P_2O_5$ in a total amount of up to 10% by weight.

7. A glass detecting device as claimed in claim 6, which comprises several glass plates of different chemical composition.

8. A glass detecting device as claimed in claim 6, wherein the exposable surface of the glass plate or plates is in each case at least 0.25 cm$^2$, preferably at least 0.5 cm$^2$.

9. A glass detecting device as claimed in claim 6 wherein the one or more glass plates are framed.

10. A glass detecting device as claimed in claim 6 wherein the glass plates have a thickness of 0.25 to 1 mm.

* * * * *

UNITED STATES PATENT AND TRADEMARK OFFICE
CERTIFICATE OF CORRECTION

PATENT NO. : 5,075,235

DATED : December 24, 1991

INVENTOR(S) : Dieter Fuchs, et al.

It is certified that error appears in the above-identified patent and that said Letters Patent is hereby corrected as shown below:

On the title page: Item [75] Inventors:
Second inventor's name is misspelled, should be, --Helmut Patzelt--.

Signed and Sealed this

Seventh Day of December, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,075,235
DATED : December 24, 1991
INVENTOR(S) : Dieter FUCHS et al It is certified that error appears in the above-indentified patent and that said Letters Patent is hereby corrected as shown below:

Figure 1 is incorrect and should be deleted. The correct Figure 1 is attached hereto.

Signed and Sealed this

Twenty-ninth Day of March, 1994

BRUCE LEHMAN

Attest:

Attesting Officer

Commissioner of Patents and Trademarks